United States Patent
Slayton et al.

(10) Patent No.: US 9,877,791 B2
(45) Date of Patent: Jan. 30, 2018

(54) SYSTEM AND METHOD FOR VIRTUAL TREATMENTS BASED ON AESTHETIC PROCEDURES

(71) Applicant: Persais, LLC, Phoenix, AZ (US)

(72) Inventors: Michael H. Slayton, Tempe, AZ (US); Vadim Kouklev, Tempe, AZ (US)

(73) Assignee: PERSAIS, LLC, Phoenix, AZ (US)

( * ) Notice: Subject to any disclaimer, the term of this patent is extended or adjusted under 35 U.S.C. 154(b) by 25 days.

(21) Appl. No.: 15/218,883

(22) Filed: Jul. 25, 2016

(65) Prior Publication Data

US 2017/0020610 A1     Jan. 26, 2017

Related U.S. Application Data

(60) Provisional application No. 62/196,787, filed on Jul. 24, 2015.

(51) Int. Cl.
| | |
|---|---|
| *G06F 3/00* | (2006.01) |
| *A61B 34/10* | (2016.01) |
| *G06F 19/00* | (2011.01) |
| *G06F 3/0484* | (2013.01) |
| *G06K 9/00* | (2006.01) |
| *G06T 3/00* | (2006.01) |

(52) U.S. Cl.
CPC .......... *A61B 34/10* (2016.02); *G06F 3/04842* (2013.01); *G06F 19/3437* (2013.01); *G06K 9/00228* (2013.01); *G06K 9/00268* (2013.01); *G06K 9/00288* (2013.01); *G06T 3/0056* (2013.01); *A61B 2034/105* (2016.02)

(58) Field of Classification Search
CPC ............ G06F 3/04842; G06F 19/3437; G06K 9/00288; G06K 9/00268; G06K 9/00228; G06T 3/0056; A61B 34/10; A61B 2034/105

See application file for complete search history.

(56) References Cited

U.S. PATENT DOCUMENTS

| | | | |
|---|---|---|---|
| 2011/0175615 A1* | 7/2011 | Grissom | G01R 33/4804 324/315 |
| 2016/0247279 A1* | 8/2016 | Lavi | G06F 19/3431 |

* cited by examiner

*Primary Examiner* — Muhammad N Edun
(74) *Attorney, Agent, or Firm* — Quarles & Brady LLP

(57) ABSTRACT

Systems and methods provide visualization of the projected results of an aesthetic treatment, such as facial skin therapy, using an image display device and a plurality of stored transformation instructions. The system receives an input image of a subject, such as a recent portrait photograph. The system determines the aesthetic treatment to apply, retrieves the associated transformation instructions, and transforms the input image with the transformation instructions to produce a modified image that represents changes to the subject's face that are expected to occur after the selected treatment. The system may include or access a virtual treatment visualization engine that stores transformation parameters describing changes to make to the input image based on the selected treatment and other input parameters. The transformation parameters may be obtained from a model that received the selected treatment. The system may determine similarities of the subject to the model.

20 Claims, 4 Drawing Sheets

SYSTEM AND METHOD FOR VIRTUAL TREATMENTS BASED ON AESTHETIC PROCEDURES

CROSS-REFERENCE TO RELATED APPLICATIONS

This application is a non-provisional claiming the benefit of priority from U.S. Prov. Pat. App. Ser. No. 62/196,787, having the same title, filed Jul. 24, 2015, and incorporated fully herein by reference.

BACKGROUND OF THE INVENTION

The subject matter disclosed herein relates generally to systems and methods for simulating aesthetic treatments of the human body, and, more particularly, to computer-implemented simulation systems and methods that generate visual estimates of the effects of an aesthetic rejuvenation procedure on a particular subject.

Aesthetic procedures aim to improve a subject's appearance by repairing or rejuvenating skin, muscle tissue, and/or ligaments, by stimulating collagen growth or other wound healing, or by ablating or excising tissue, among other means. For example, a number of new face rejuvenating procedures join the existing approaches in the aesthetic industry every year; these may include without limitation pharmacology based topical solutions, minimally invasive and invasive surgery, and energy based treatments such as laser and other photon based systems, Intense Therapy Ultrasound (ITU), radio frequency (RF), cold (cryo), microwave, and Multiple Energy Delivery Systems (MES).

In many aesthetic procedures, such as topical or energy-based face rejuvenation, the subject does not exhibit immediate positive results from the treatment and must wait an extended period of time, potentially receiving additional treatments to complete the procedure. It would be advantageous to provide, approximate the time of treatment, an estimate to the subject of the expected results after a certain amount of time has passed. Before and after graphics of previously treated subjects are known, but the current subject would best be served seeing the projected results on his/her own image.

A wide variety of procedures may exist for achieving a certain aesthetic goal. Furthermore, each procedure may have a number of treatment options, and the treatment options may have their own parameters. Not all of the choices may be effective for a particular subject, considering the subject's unique physical composition. It would be advantageous to provide the subject with estimated results from the various procedures to aid in the selection of (a) suitable procedure(s).

BRIEF DESCRIPTION OF THE INVENTION

The present disclosure overcomes the aforementioned drawbacks by providing systems and methods that simulate the effect of one or more treatments on a subject to produce projected results, and then display the projected results as one or more images of the subject treatment area. The system first learns to identify results using photos taken during the treatment of model subjects. The system compares identifiable features in the treatment area of the model subject across photographs, generating data describing the differences between photographs. The system associates this data with the treatment parameters and the model subject's physical attributes, and stores the associated data in a virtual treatment database.

The system then analyzes an actual subject by collecting the subject's current photo and attributes and comparing the attributes to the model subjects in the database. For a matching model subject, the system manipulates the actual subject's photo according to the described differences in the matching model subject's photos. The system presents the manipulated image(s) of the actual subject as projected results of the one or more treatments that were applied to the matching model subject.

In one embodiment, the present disclosure provides a computing device for electronically generating virtual treatment results of a subject. The computing device includes memory storing program instructions and one or more sets of treatment parameters, each of the one or more sets being associated with a corresponding aesthetic procedure of a plurality of aesthetic procedures; and, a processor that accesses the memory. The processor executes the program instructions to: receive a baseline image depicting a first treatment area of a subject; identify, based on the corresponding treatment parameters of a first set of the one or more sets of treatment parameters, one or more zones of the baseline image, the first set being associated with a first aesthetic procedure of the plurality of aesthetic procedures; transform the baseline image within the one or more zones using the first set of treatment parameters to produce a first post-treatment image that depicts an estimated appearance of the first treatment area after the first treatment area is treated with the first aesthetic procedure; and display the baseline image and the first post-treatment image to the user.

To identify the one or more zones, the processor may execute the program instructions to: detect a face in the baseline image; detect a plurality of fiducial points on the baseline image based on the detected face; and juxtapose the face with a deformable vector model comprising a plurality of polygons and a plurality of polylines defining vertices of the vector model, the vertices including the plurality of fiducial points, to produce the one or more zones. To transform the baseline image within the one or more zones, the processor may execute the program instructions to: identify a plurality of feature zones associated with the first aesthetic procedure; determine that a first feature zone of the plurality of feature zones corresponds to a first zone of the one or more zones of the baseline image; and modify image data of the baseline image within the first zone using a sequence of image manipulation techniques identified by the first set of transformation parameters, the sequence of image manipulation techniques being associated with the first feature zone. The image manipulation techniques may include: a directional local filtration and a subsequent high frequency restoration of some or all of the image data; and, a distortion effect to move the image data at an edge of a first zone of the one or more zones.

The processor may produce the first post-treatment image to depict the estimated appearance of the first treatment area a first period of time after the first treatment area is treated with the first aesthetic procedure, and may further execute the program instructions to: transform the baseline image within the one or more zones using the first set of treatment parameters to produce a second post-treatment image that depicts the estimated appearance of the first treatment area a second period of time after the first treatment area is treated with the first aesthetic procedure, the second period of time being longer than the first period of time; and display the baseline image, the first post-treatment image, and the second post-treatment image to the user sequentially to show a treatment progression of the first aesthetic procedure results. The memory may further store a set of aging parameters, and the processor may further execute the program instructions to: identify, based on the set of aging parameters, one or more aging zones of the baseline image; transform the baseline image within the one or more aging zones using the set of aging parameters to produce a first aged image that depicts aging effects accumulated on the first treatment area during the first period of time after the baseline image was captured, and a second aged image that depicts aging effects accumulated on the first treatment area during the second period of time after the baseline image was captured; and display a user interface containing a plurality of virtual procedure images including the baseline image, the first post-treatment image, the second post-treatment image, the first aged image, and the second aged image, the user interface enabling a user of the computing device to view an aging progression and the treatment progression by changing which of the plurality of virtual procedure images is displayed.

The computing device may further comprise a display and a user input device each in communication with the processor, and the processor may further execute the program instructions to present a user interface to the user via the display and the user input device, the user interface enabling the user to provide user input to the processor. The user input may be a modification to the one or more zones, and responsive to receiving the user input, the processor may execute the program instructions to adjust a perimeter of a first zone of the one or more zones according to the user input. The user input may be a treatment goal, and responsive to receiving the user input, the processor may execute the program instructions to determine that the first aesthetic procedure is associated with the treatment goal. The first set of treatment parameters may be determined to transform a pre-treatment image into a post-treatment image, the pre-treatment image depicting a treatment area of a model and captured before the treatment area is treated with the first aesthetic procedure, and the post-treatment image depicting the treatment area of the model and captured after the treatment area is treated with the first aesthetic procedure.

In another embodiment, the present disclosure provides a system that includes a server storing a virtual treatment knowledge base, and a program application installed on a plurality of user devices in electronic communication with the server, the program application configuring each of the plurality of user devices to cooperate with the server to create a virtual treatment procedures platform. The program application further configures a first user device of the plurality of user devices to: receive a baseline image depicting a first treatment area of a subject; transform the baseline image using a plurality of transformation parameters to produce a first post-treatment image that depicts an estimated appearance of the first treatment area after the first treatment area is treated with a first aesthetic procedure; and display the baseline image and the first post-treatment image on the first user device. The server may further store a virtual treatment learning engine that, when executed, configures the server to: receive a pre-treatment image depicting a second treatment area of a model before the second treatment area is treated with the first aesthetic procedure; receive a post-treatment image depicting the second treatment area after the second treatment area is treated with the first aesthetic procedure; determine that the plurality of transformation parameters transforms the pre-treatment image into the post-treatment image; and, store the plurality of transformation parameters in the virtual treatment knowledge base. The program application may further configure the user devices to receive the plurality of transformation parameters from the server.

The program application may further configure the first user device to receive identifying information of the subject and send the identifying information to the server, and the server may be further configured to determine, based on the identifying information, that the subject is similar to the model, and, responsive to a determination that the subject is similar to the model, send the plurality of transformation parameters to the first user device. To receive the identifying information, the program application may configure the first user device to retrieve the identifying information from a source that is external to the system and is in electronic communication with the first user device.

The system may further include a practices registry implemented as an electronic data store accessible by the server, the practices registry including a plurality of practice records each associated with a corresponding practice of a plurality of practices that perform the first aesthetic procedure and are located in a selected geographic area; the server may be configured to retrieve practice information from one or more of the plurality of practice records and send the practice information to the first user device. A second user device of the plurality of user devices may be controlled by a first practice of the plurality of practices, and the program application may further configure the first user device to: receive a first user input on an input device of the first user device; determine that the first user input is a request to view the practice information; receive the practice information from the server; display the practice information on a display of the first user device; receive a second user input on the input device; determine that the second user input is a selection, from the practice information, of an offer by the first practice to perform the first aesthetic procedure; and communicate with the second user device to schedule an appointment for the subject with the first practice.

The program application may configure the first user device to, prior to transforming the baseline image, receive a first user input on an input device of the first user device, determine that the first user input comprises one or more treatment goals, and determine that the first aesthetic procedure is associated with the one or more treatment goals.

In yet another embodiment, the present disclosure provides a method performed by a computing device for providing an electronic visualization of a virtual treatment on a treatment area of a subject. The method includes: receiving a baseline image depicting the treatment area; receiving a plurality of transformation parameters associated with an aesthetic procedure; transforming the baseline image using the plurality of transformation parameters to produce a first post-treatment image that depicts an estimated appearance of the treatment area after the treatment area is treated with the aesthetic procedure; and displaying, in a user interface of the computing device, the baseline image and the first post-treatment image. Receiving the plurality of transformation parameters may include: determining an identifying parameter of the subject; matching the identifying parameter of the subject to a model identifying parameter stored in a model treatment results record, the model treatment results record storing a plurality of model transformation parameters for transforming a pre-treatment image of the model to a post-treatment image of the model; and, obtaining the plurality of model transformation parameters as the plurality of transformation parameters.

The method may further include: before receiving the plurality of transformation parameters, receiving a first user input comprising one or more treatment goals and determining that the one or more treatment goals are associated with the aesthetic procedure and with a plurality of potential aesthetic procedures; receiving a plurality of sets of potential transformation parameters, each set associated with a corresponding potential aesthetic procedure of the plurality of potential aesthetic procedures; transforming the baseline image using each set of the plurality sets of potential transformation parameters to produce a corresponding potential post-treatment image of a plurality of potential post-treatment images each depicting the estimated appearance of the treatment area after the treatment area is treated with the corresponding potential aesthetic procedure; further displaying, in the user interface of the computing device, the plurality of potential post-treatment images, the user interface enabling a user of the computing device to select one or more of the baseline image, the first post-treatment image, and one or more of the plurality of potential post-treatment images for display; receiving a second user input that is a selection of the first post-treatment image; and sending, to a server in electronic communication with the computing device, information identifying the subject and the aesthetic procedure.

BRIEF DESCRIPTION OF THE DRAWINGS

The present invention will become more apparent from the detailed description set forth below when taken in conjunction with the drawings, in which like elements bear like reference numerals.

DETAILED DESCRIPTION OF THE INVENTION

Figure 1:
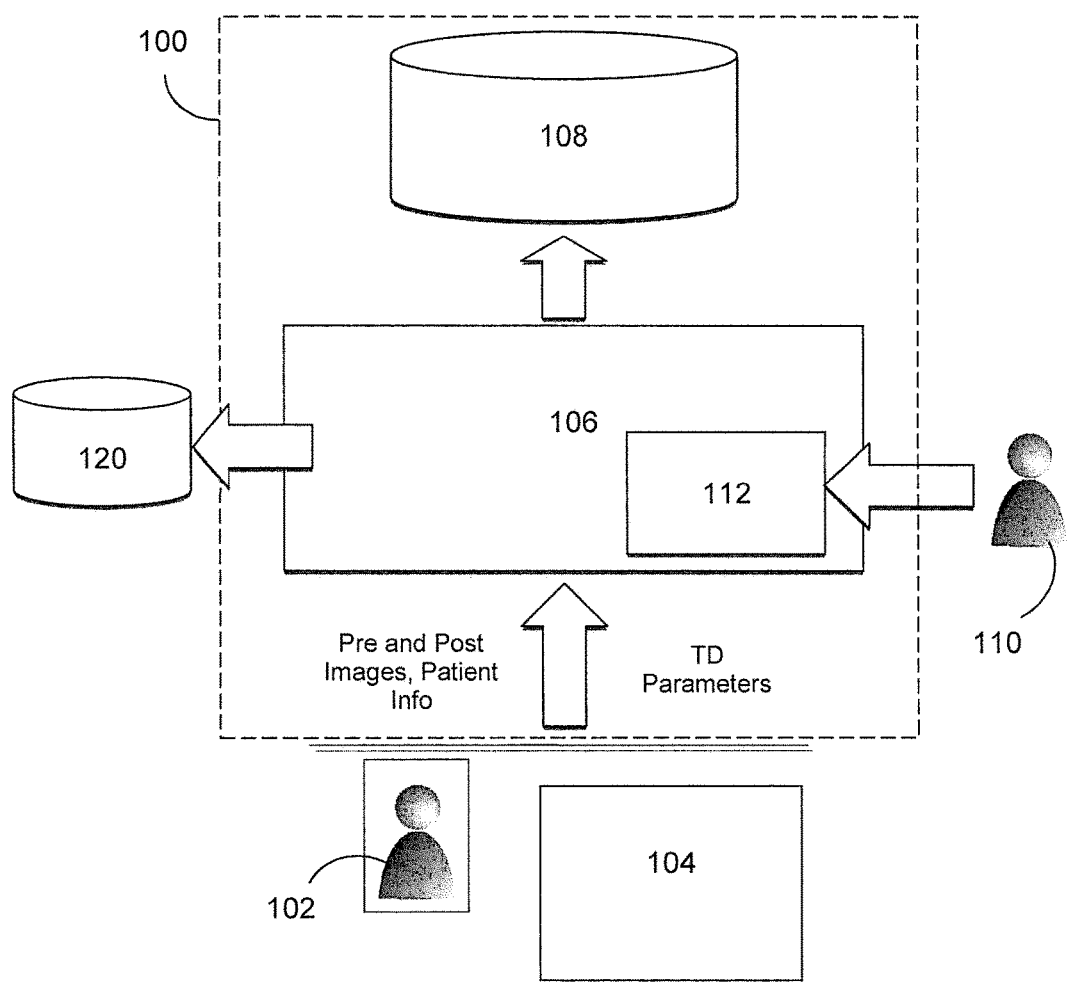
FIG. 1 is a schematic diagram of an example learning component of a system in accordance with the present disclosure.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures depict selected embodiments and are not intended to limit the scope of embodiments of the invention. Skilled artisans will recognize the examples provided herein have many useful alternatives and fall within the scope of embodiments of the invention.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically, such as when elements or features are embodied in program code. Thus, although the figures depict example arrangements of processing elements, additional intervening elements, devices, features, components, or code may be present in an actual embodiment.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, diodes, look-up tables, etc., which may carry out a variety of functions under the control of one or more microprocessors or other control devices. Other embodiments may employ program code, or code in combination with other circuit components.

In accordance with the practices of persons skilled in the art of computer programming, the present disclosure may be described herein with reference to symbolic representations of operations that may be performed by various computing components, modules, or devices. Such operations may be referred to as being computer-executed, computerized, software-implemented, or computer-implemented. It will be appreciated that operations that can be symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

As non-limiting examples unless specifically indicated, any database or data store described herein may comprise a local database, online database, desktop database, server-side database, relational database, hierarchical database, network database, object database, object-relational database, associative database, concept-oriented database, entity-attribute-value database, multi-dimensional database, semi-structured database, star schema database, XML database, file, collection of files, spreadsheet, or other means of data storage located on a computer, client, server, or any other storage device known in the art or developed in the future. File systems for file or database storage may be any file system, including without limitation disk or shared disk, flash, tape, database, transactional, and network file systems, using UNIX, Linux, Mac OS X, Windows FAT or NTFS, FreeBSD, or any other operating system.

The various aspects of the invention will be described in connection with providing a virtual aesthetic treatment for a subject by projecting results of the treatment onto one or more images of the subject. That is because the features and advantages that arise due to the invention are well suited to this purpose. However, it should be appreciated that the invention is applicable to other procedures and to achieve other objectives as well.

Generally, a system in accordance with the present disclosure may include one or more computing devices and one or more data stores configured to implement a learning component and a visualization component of the system. The learning component may be executed to develop a database of model treatment results. The model treatment results describe a number of models (i.e., persons that received one or more treatments) and the actual results of treatments applied to the models. The visualization component may be executed to generate projected results of a particular treatment applied to a subject (i.e., a person receiving or considering receiving the particular treatment). The projected results may be in the form of one or more images of the subject that are manipulated according to model treatment results for a model that has similar physical characteristics to the subject and received the same or a similar treatment.

A model treatment result may be represented by a collection of data elements, such as a data structure or a record for storage in a database. Each model treatment result record may be associated with the model and the treatment applied to the model. FIG. 1 illustrates a learning component 100 of the system. To collect the model treatment results a number of models 102 may be treated with a therapeutic device (TD) 104. The TD 104 may be any suitable therapeutic device for performing one or more of the aesthetic procedures to be simulated by the system. Non-limiting examples of a TD 104 include: machines, including machines that apply photonic energy (e.g., intense pulsed light (IPL) devices and other laser devices, light-emitting diodes (LEDs)), sonic or ultrasonic energy (e.g., Intense Therapy Ultrasound (ITU)), radio frequency (RF) energy, thermal (including cryogenic) energy, microwaves, mechanical energy (e.g., percussive, massage, and other contact-based devices), or a combination of different energies (e.g., Multiple Energy Delivery Systems (MES)); ointments and other topical compositions; surgical tools; physical therapy regimens such as massage and exercise; medications and ingestable supplements; and the like.

Non-limiting examples of conditions, which may be located anywhere on the body, that the aesthetic procedure(s) applied by the TD 104 is/are directed to treat include: skin conditions such as acne, rosacea, scars, lesions, hypo- or hyperpigmentation, purpura, and the like; cellulite and other fatty deposits; tattoos (i.e., tattoo removal); unwanted hair; baldness; tooth discoloration; sagging (i.e., loose skin, such as in the chin or arms, or loose muscle fibers, such as in the breast); and the like. The TD 104 may be a professional device for use by professionals only. A trained physician or cosmetology practitioner must apply the professional device to the model 102 in a controlled environment of a medical or therapeutic facility. The TD 104 may alternatively be a retail device for home use by subjects without any professional supervision. In some embodiments, a set of therapeutic devices 104 may be applied in combination to perform the aesthetic procedure.

The TD 104 may have device parameters, such as internal device settings (e.g., energy fluence, intensity, or density, number of lines (e.g., in an ultrasound procedure), points of treatment, procedures) used during treatment, that describe the state of the TD 104 when it delivered the treatment. The TD 104 may also define treatment parameters, such as application times and intensities, and the like. Where a set of multiple TDs 104 are applied, the device and/or treatment parameters may include such parameters from each applied TD 104. The device parameters and treatment parameters may be recorded in the model treatment result record. The model's 102 personal physical characteristics, including skin type, age, medical conditions, race, and other characteristics that may be relevant to the efficacy of the treatment (e.g. medical condition, treatment history), may be recorded in the model treatment result record. Additional parameters of the model 102 include the treatment area, which is the area of a body part that is affected by the treatment. The treatment area may include the area that directly receives treatment (e.g., ultrasound energy), as well as surrounding tissue that is affected, such as due to a biocascade caused by the treatment.

Images of the treatment area on the model 102, taken in a controlled environment, may also be stored in the model treatment result record. These images may be captured before the treatment, right after the treatment, and several times in some extended period after the treatment, as needed to depict the results of the treatment on the model 102. The images may be captured as still photographs, such as with a camera, or the images may be frames extracted from a video. The images may be analyzed to determine one or more image modification parameters (IMPs), which are coefficients tied to different zones on the image and used to manipulate the subject's baseline image as described below. The IMPs may be stored with the images in the model treatment result record.

A virtual treatment learning engine (VTLE) 106 is a system module that may receive the parameters that originate from the models 102 and TD 104. The VTLE 106 may also compute any additional parameters, such as IMPs for the images. For calculating IMPs, the VTLE 106 may be configured to execute an image modification estimation algorithm (IMEA). The IMEA, generally, may compare images of the treatment area taken at different points during the treatment, and may identify changes in the treatment area present in the newer image as compared to the older image. In an implementation, the IMEA may identify the changes between pre-treatment images and post-treatment images using a vector model. In one implementation, the vector model may be stored in the VTKB 108 or another data store for vector models. Such a vector model data store may contain one or more vector models for each treatment area (e.g., body part) that can be virtualized by the present system. The vector model may store data that describes the body part in any suitable format for enabling vector-based graphics, such as a text file using vectors structured as YAML or another data serialization format.

The vector model may be composed of vectors formed into polygons and polylines that delineate one or more zones of an image. The zones may correspond to regions within the treatment area that may be changed by the aesthetic procedure. For example, a vector model for a face may delineate zones for cheeks, lips, forehead, eyebrows, etc., as illustrated by example in FIGS. 3 and 4. Other zones may correspond to regions that the treatment area should not affect, such as zones containing certain nerve structures or other sensitive anatomy. The VTLE 106 may compare the pre-treatment image with the vector model, such as by juxtaposing the pre-treatment image and the vector model, or by overlaying the vector model on the pre-treatment image. From this comparison, the VTLE 106 may modify the vectors of the vector model to produce a set of pre-treatment contours, which are polygons and polylines that represent the actual shape, size, path, etc. of the relevant zones displayed in the pre-treatment image.

The VTLE 106 may then perform the same comparison of the post-treatment image with the vector model, producing a set of post-treatment contours that represent the actual shape, size, path, etc. of the relevant zones displayed in the post-treatment image. The VTLE 106 may compare the post-treatment contours to the pre-treatment contours and extract values indicating the differences between the sets of contours. These values demonstrate changes in any of the zones, such as shifts in location, size, shape, or orientation, from the pre-treatment image to the post-treatment image.

The VTLE 106 may store these values, with an identification of the zones that changed, in the model treatment results record.

The VTLE 106 may further obtain texture samples of each image within some or all of the zones. The textures may be sampled using a set of estimation functions applied to a matrix of pixels taken from the desired area of the image. The estimation functions may be any suitable texture sampling functions. In some implementations, the results of a function may be a scalar value or a set of scalar values that describe a certain texture feature. In some implementations, the results of a function may be a classification of a texture feature. Texture sampling functions may be configured to detect properties of the skin, such as blemishes, hair follicles, pores, etc., in a statistically significant manner according to the resolution of the image. The texture samples may be taken from the zones of the vector model or from the zones delineated by the contours obtained as described above, and may in particular be taken from the zones of interest (i.e., the zones that changed from pre- to post-treatment). The texture samples may be taken from the pre-treatment image and the post-treatment image. The texture samples of corresponding zones (i.e., the same zone in the pre-treatment and post-treatment image) may be compared, from which the VTLE 106 may extract the differences between textures as values that represent changes in appearance of the treatment area between pre- and post-treatment.

The IMEA may additionally include configurations that account for ambient changes in the image attributes between the pre-treatment image and the post-treatment image. For example, the ambient lighting conditions present when each photo is taken of the treatment area may be different. The VTLE 106 may perform an image histogram comparison or other analysis to identify an overall difference in the image that the IMEA might identify as a value to be extracted, but which is not actually a difference in the treatment area. The VTLE 106 may adjust the image parameters to reduce or negate such changes, such as by tuning the color balance of the post-treatment image to match that of the pre-treatment image.

A VTLE coach 110 or other administrator of the system may confirm the accuracy of the IMPs calculated by the IMEA, or may unilaterally calculate and input the IMPs. A training tool 112 installed within the VTLE 106 may be used to modify, add, or remove IMPs. The training tool 112 may also be used to tune other parameters of the model treatment result record. For example, the training tool 112 may be used to adjust the contours identified by the VTLE 106. The VTLE 106 may further query one or more external sources 120 to obtain additional parameters related to the images of the model. For example, if the model's age is not provided, the VTLE 106 may send one of the images of the model to a service operating an age detection algorithm, and may receive a projected age of the model from the service.

Once any confirmations or additional data are input by the VTLE coach 110, the VTLE 106 may store all of the parameters in a record for the model treatment result in a virtual treatment knowledge base (VTKB) 108, which may be a centralized (e.g., stored on the local device or hardcoded into a software application implementing the system) or distributed data store configured for storing the relevant data for each aesthetic procedure and each model that underwent one of the procedures. In some implementations, the VTKB 108 may store, for each of the model treatment result records, facts and rules that together describe the processes required to transform an earlier image of the model to a later image of the model (e.g., a pre-treatment image to a post-treatment image). The system may later follow the description of processes to transform a baseline image of a subject into an image showing the projected results of a procedure.

The facts in a record may include any of the collected or computed data elements described above, including the model parameters (age, race, etc.), treatment parameters, pre- and post-treatment model images, IMPs (including lists of IMA(s) as described below), identified zones (including zones of interest), and the like. The rules in a record may control aspects of the IMP generation for the associated model. The rules may be stored in the record, or the rules may be stored in a rules database in the VTKB 108 and the result record may include a reference to each rule. A rule may be created during the learning process (i.e., creation of a model treatment result record), either automatically upon recognition of certain features of the treatment area, or by the VTLE coach 110. The rule may be a simple conditional statement, and may further be supported by some production systems or implemented in cognitive architectures like Soar. Non-limiting exemplary if/then conditional rules are:

IF subject is very thin faced (e.g., distance between cheek zones is less than a threshold) THEN do not use IMA "CHEEK LIFT" for zones "LEFT CHEEK" and "RIGHT CHEEK";

IF subject skin type is AA THEN coefficients for IMA "EYE BAG WHITENING" must be in the range (0.4, 0.6) for zones "LEFT EYE BAG" and "RIGHT EYE BAG".

The VTKB 108 may further include a presets database storing one or more presets. A preset is a list of rules and/or parameters created for a particular mode (i.e., set of treatment parameters) of each TD 104 which is to be virtualized. For example, a TD 104 that applies energy to the face for performing aesthetic procedure might have two protocols: "FULL FACE PROTOCOL" that treats the entire face, such as in a facelift; and "NECK ONLY PROTOCOL" that only treats the neckline. A preset for each protocol may be created, and non-limiting examples of rules in the presets may be stored as follows:

IF "FULL FACE PROTOCOL" preset is active THEN
APPLY IMA "CHEEK LIFT" TO ZONE "LEFT CHEEK" PARAMETERS (X=1, Y=2)
APPLY IMA "CHEEK RIGHT" TO ZONE "RIGHT CHEEK" PARAMETERS (X=0.1, Y=2.2, Z=3)
APPLY IMA "SMOOTH" TO ZONE "NECK" PARAMETERS (X=0.1, Y=2.2, Z=3)
IF "NECK ONLY PROTOCOL" preset is active THEN
APPLY IMA "SMOOTH" TO ZONE "NECK" PARAMETERS (X=0.1, Y=2.2, Z=3)

Thus, presets may be said to map the TD 104 settings to a set of desired IMPs for the associated treatment. The model treatment result record may include references to the presets for the treatment mode associated with the record. Multiple presets can be associated with a single model treatment result record. This might be needed when multiple devices are used in a combination therapy or when there are two or more independent sets of settings for a single system. For example, the TD 104 that supports "FULL FACE" and "NECK ONLY" area protocols may also provide that each of them can be done at "HIGH ENERGY" or "LOW ENERGY" settings. Additional "HIGH ENERGY" and "LOW ENERGY" presets can be stored, and a model treatment result record may identify both the area preset and the energy preset to be used.

Figure 2:
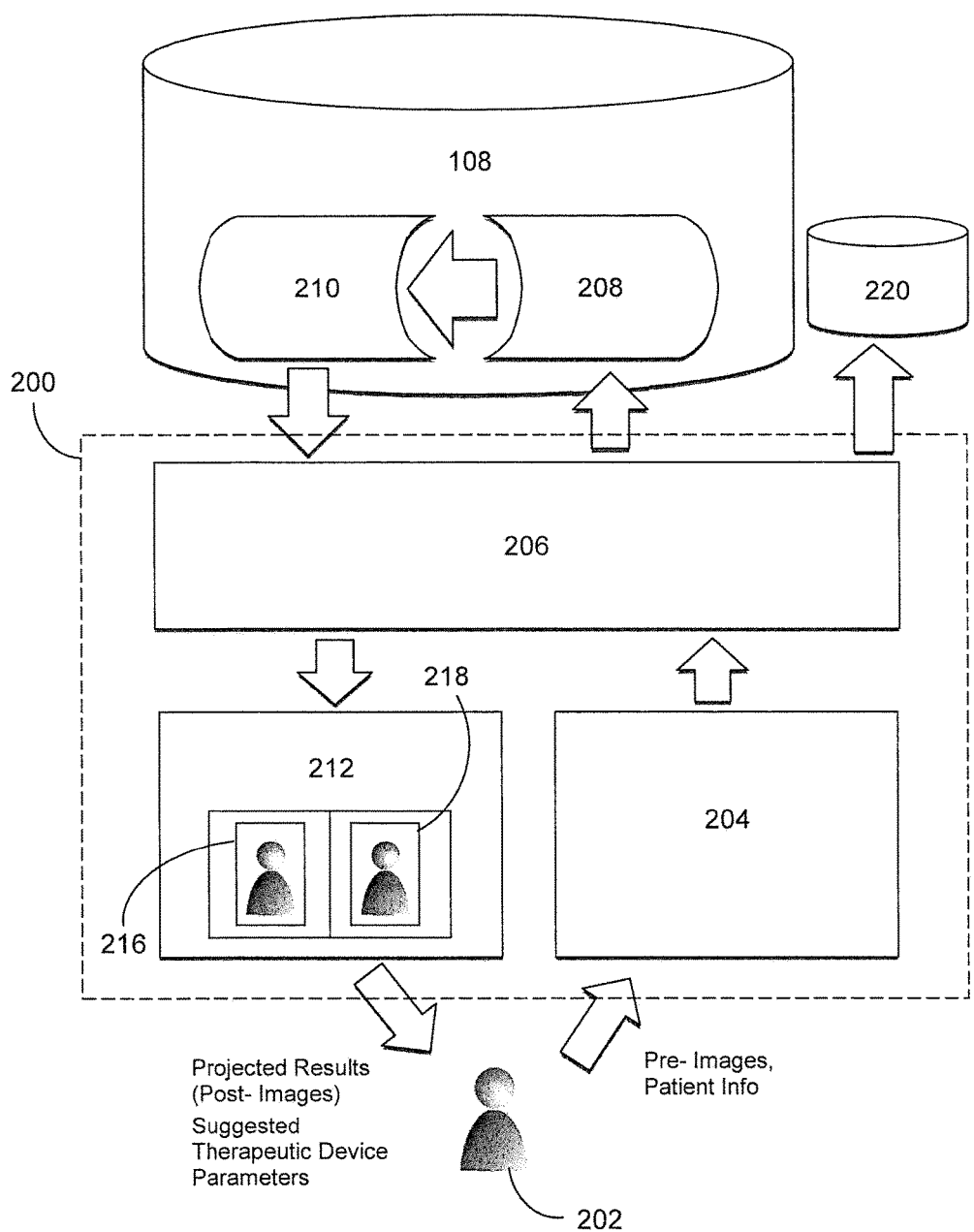
FIG. 2 is a schematic diagram of an example visualization component of a system in accordance with the present disclosure.

FIG. 2 illustrates a visualization component 200 of the system. The visualization component 200 may include a data entry module (DEM) 204 that collects images of a subject's 202 body parts to be treated (i.e., treatment areas), along with the subject's 202 personal information related to the treatment (skin type, age, medical conditions, race, and other characteristics collected for the models 102). The DEM 204 may present a user interface on a user device and collect, as the images and other data, input provided to the user interface by a user, which may be the subject 202, a physician, the VTLE coach 110, etc. The images may be input in any suitable format, including known image formats such as .GIF and .BMP, as well as in video format. The DEM 204 delivers the collected subject 202 data to a virtual treatment visualization engine (VTVE) 206. The VTVE 206 may further query one or more external sources 220 to obtain additional parameters related to the subject or the baseline images collected by the DEM 204. For example, if the subject's age is not provided, the VTVE 206 may send one of the baseline images to a service operating an age detection algorithm, and may receive a projected age of the subject from the service.

The VTVE 206 may use the provided and collected information to find a closest matching model treatment result record in the VTKB 108. In particular, the VTVE 206 may query the VTKB 108 using the subject data 208 to look up parameters and rules in the model data 210 (including the model treatment result records) that might be best fitted for the current subject 202 using information provided by the user as search optimization parameters. The VTKB 108 may also use the subject's 202 baseline image to extract some attributes, which can refine the search for a matching model treatment result record. In one implementation, the records of the VTKB 108 may include one or more parameters that are anthropometrically linked to sub-populations of humans. For example, skin pigmentation and/or measurements of facial features can identify a common ethnicity, race, or phenotype of a subset of the models. The VTKB 108 may determine that attributes of the subject match these parameters and may limit the search to the associated subset of model treatment result records. In another implementation, the records of the VTKB 108 may include a parameter identifying a skin type of the associated model, the skin type being selected from a finite list of skin types. The skin type of the subject may be determined from the skin texture parameters of the baseline image, and the VTKB 108 may search only the subset of model treatment result records that contain the same skin type.

Receiving a match or close match, the VTVE 206 may extract the IMPs from the matching model treatment result record (alternatively, the VTKB 108 may return only the IMPs to the VTVE 206). The VTVE 206 may then execute the virtual treatment procedure, in which the IMPs are used to manipulate the baseline image of the treatment area of the subject 202, producing one or more estimated post-treatment images that represent the projected results of the treatment on the subject 202. The VTVE 206 may be configured to apply multiple processes to generate the projected results. In one implementation, the VTVE 206 may execute a zone detection algorithm (ZDA) that extracts image data from the baseline image and identifies zones of the image that may correspond to the expected treatment area(s) of the subject 202. In one implementation, the ZDA may identify all potential zones in the baseline image, which collection of zones may be subsequently parsed to retain only those zones that can be associated with either (1) a treatment area identified in the treatment parameters, or (2) an IMP of the matching model treatment result record. In another implementation, the treatment parameters may include descriptions of the treatment areas that are targeted for aesthetic improvement, and the ZDA may associate these descriptions with the baseline image to determine the zones that pertain to the treatment and, thus, should be identified by the ZDA. In another implementation, the IMP(s) of a model treatment result record may describe the treatment areas and the ZDA may associate each IMP with the baseline image to determine the zones.

Figure 3:
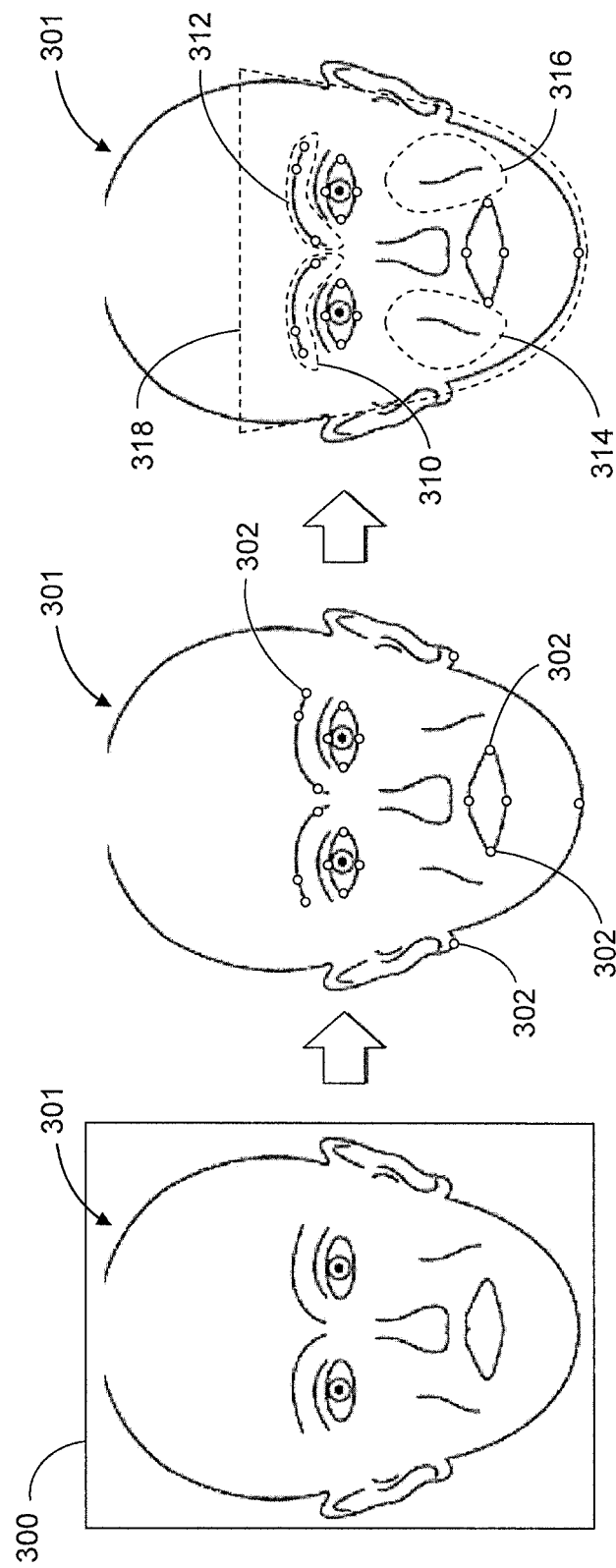
FIG. 3 is a diagram showing zones of an image identified by an exemplary zone detection algorithm.

Referring to FIG. 3, an exemplary implementation of a ZDA detects zones on a baseline image 300 of the subject's face 301. A face detection algorithm may first detect the face 301 in the image. The face detection algorithm may be a Viola-Jones object detection or another suitable algorithm, and may be implemented in any suitable framework, such as OpenCV. The ZDA may then detect fiducial points 302 (e.g., around eyes, mouth, etc.) using a trained classifier, such as a cascade classifier (e.g., in OpenCV). The ZDA then may juxtapose the detected face with a vector model 318 of face features (composed of polygons and polylines) using the fiducial points 302 as some or all of the vertices, or as reference points for the locations of some or all of the vectors in the vector model. The ZDA may further use gradient and color properties of the baseline image 300 to determine the configuration of the vector model 318. The vector model 318 may be one or a set of parametric deformable models. The result of the comparison may be a set of zones 310, 312, 314, 316 composed of polygons and polylines as described above with respect to the application of the IMEA. In one implementation, the ZDA may be a face tracker working with gray scale images and adaptive with respect to gradient properties of the baseline image 300. The face tracker may be extended to take into account color properties and anthropometric parameters of zones of interest (e.g., face, neck etc.). The different zone 310-316 detection processes may be applied in combination as described, either sequentially or in parallel, or a single one of the processes may be applied by the ZDA if sufficient to detect the desired zones 310-316 for manipulation.

Figure 4:
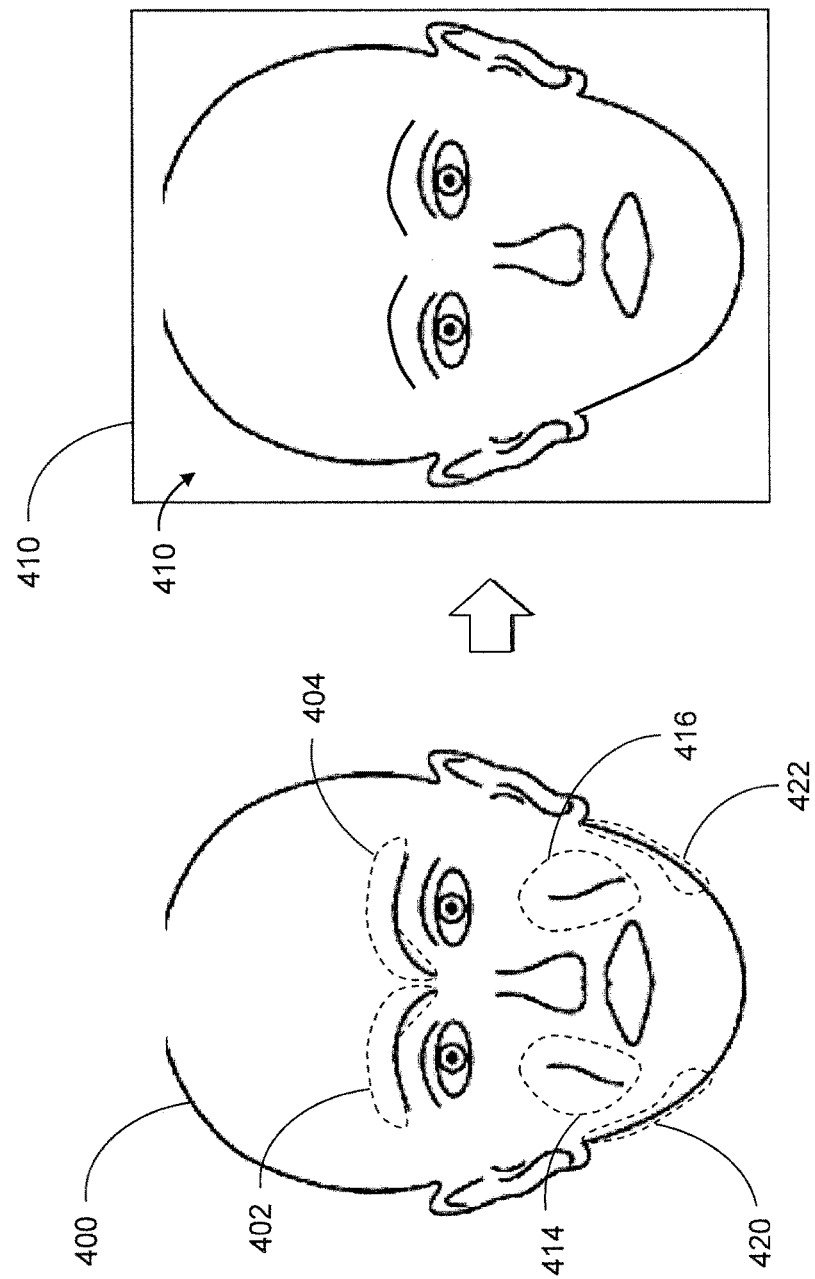
FIG. 4 is a diagram showing zones of an image identified by an exemplary image modification algorithm.

In some implementations, the VTVE 206 may execute an image modification algorithm (IMA), which may be a set of algorithms for modifying different zones 310-316 (i.e., some or all of the zones 310-316 identified by the ZDA) of the baseline image 300. The zones 310-316 to be modified may be identified by the IMPs of the matching record, and the appropriate IMA for modifying the zones 310-316 of interest may be selected. In some implementations, the IMPs may include the IMA(s) as a list of image processing methods to be applied to the baseline image 300, and a set of rules specifying the order and parameters of the processing methods. Referring to FIG. 4, the IMA may identify one or more feature zones of an image for manipulation. The feature zones may correspond to some or all of the treatment areas that are targeted by the particular treatment. Some or all of the feature zones may further correspond to some or all of the zones delineated by the ZDA. In a non-limiting example, the feature zones on a face 400 may include eyebrow zones 402, 404, cheek zones 414, 416, and jaw zones 420, 422. In one implementation, the feature zones may be identified by interpreting the IMPs of the matching model treatment results record. For each feature zone of interest, the VTVE 206 uses the IMPs to identify the zone, the image processing methods to apply to the zone, and the parameters and parameter values to pass to the image processing method to transform the portion of the baseline image inside the zone.

The IMA set of algorithms may include existing image manipulation techniques such as texture smoothing, zone distortion, color normalization, anatomy specific filtration, and the like. Various image manipulation techniques may be applied to the image within each of the feature zones. The techniques to be applied may depend on the characteristics of the treatment and of the feature zone being manipulated. For example, in a facelift procedure a cheek zone 414, 416 may be targeted to reduce or eliminate deep "smile lines." The IMA may apply directional local filtration to smooth down wrinkles and then restore some of the high frequency features of the skin texture back to the processed image to make it look more natural. In another example of a facelift procedure, a jaw zone 420, 422 may be targeted to eliminate fat or excess skin. In one example, the IMA modifies a cheek zone along with surrounding face image background by shifting and stretching the selected cheek zone; the direction and degree of the change is defined by IMPs (as specified at the learning stage). The IMA may then apply a distortion effect to move the edge a desired distance toward, e.g., the nose, essentially narrowing the jawline as illustrated.

In deforming the selected feature zones, the IMA may blend the feature zones with the surrounding image. The blending may into account the feature zone size and shape, the chromatic values and chromatic distribution of the pixels, and the IMPs that govern the image modifications. The deformations produce a post-treatment image 410 of the subject, which depicts the estimated appearance of the treatment area (e.g., the face 410) after the aesthetic procedure is applied. A number of estimated post-treatment images can be generated to illustrate different aspects of the treatment(s) and/or projected results. In one example, an image may be generated for each of multiple different treatment levels (i.e., sets of parameters) available for the selected aesthetic procedure. In another example, a post-treatment image may be generated for each of a plurality of potential aesthetic treatments. In another example, an image may be generated for each of multiple durations of elapsed time from the treatment. Where multiple estimated post-treatment images are generated, each image may be generated from the baseline image by applying the IMPs that correspond to the desired treatment parameters and/or projected results. That is, a 30-day image and a 60-day image may each be generated directly from the baseline image using stored IMPs for 30- and 60-day elapsed time periods. Additionally or alternatively, where sequential estimated post-treatment images are appropriate (e.g., the 30-day and 60-day example), subsequent post-treatment images may be generated from one or more of the previous post-treatment images.

In another example, the transformation parameters may include parameters for an aging process. That is, the above methods may be used to "age" the subject in the baseline image based on a specified period of time elapsed after the baseline image was captured. The aging procedure, or aging transformation parameters, may be applied to transform the baseline image together with transformation parameters for one or more aesthetic procedures, or in absence of any virtualization of an aesthetic procedure. Thus, the above systems and methods may be used to produce aged images that show the subject an estimated aging progression of her appearance if she does not receive the aesthetic procedure(s).

The estimated post-treatment images may be generated in any suitable format. In one implementation, the estimated post-treatment images may be static images, perhaps calculated for a specified date in the future. For example, if the subject 202 is interested in how she will look in 30, 60, and 90 days after treatment, there will be three images generated and presented, one for each time interval. In another implementation, the estimated post-treatment images may be dynamic images (e.g., animated .GIFs) or a video. For example, if the subject is interested in how she will look in 30 days, there can be a single image generated for each hour of this term and all these 720 images can be shown with a short delay between them as a video to illustrate a projected gradual process of transformation for a treated body part. To minimize the amount of calculations required, generic image morphing techniques may be used to generate some intermediate frames. In another example, the user may input a real-time video of the subject, such as a direct feed from a video camera that is filming the subject, and the output may be the same video modified to show the estimated post-treatment images.

Once the estimated post-treatment images are generated, the VTVE 206 may deliver the estimated post-treatment images to a data visualization module (DVM) 212 that is configured to generate interface screens containing the projected results, and to deliver the interface screens to a user interface on a user device, such as a tablet or desktop computer. The DVM 212 may arrange the interface screens in any suitable format such that the user can view the projected results. In one implementation, the DVM 212 may display the baseline image 216 next to one or more of the estimated post-treatment images 218 to demonstrate the projected results. The DVM 212 may be in communication with the DEM 204, and the DEM 204 may enable the user to modify the estimated post-treatment images, such as by adjusting the perimeter and/or location of one or more zones and/or of one or more fiducial points, as described above with respect to the training tool 112.

In some implementations, after the subject 202 has received the treatment(s), the accuracy of the projected results may be verified. The user or another entity may input a confirmation that, at an elapsed time after the treatment(s), the subject 202 appearance is similar to the estimated post-treatment image that corresponds to the elapsed time. The input may be a simple check-box submission, a message, or another textual or form-based confirmation. Additionally or alternatively, the confirmation may be a new photo of the treatment area(s) of the subject. The system may compare the new photo to the corresponding estimated post-treatment image and determine that the projected results were achieved. If the projected results prove accurate (e.g., to a certain threshold), the VTLE 106 may add the treatment results to the VTKB 108 as one of the model treatment result records.

In consideration of the above, a system implementing the virtual therapy procedures may be implemented using any suitable processing and storage configuration or combinations thereof. In one implementation, a processing configuration for the received and generated data may be performed solely on the user's device, and may be in a single program application adapted for the user device. Non-limiting examples of such applications include a mobile application (e.g., for mobile devices running iOS, Android, etc.), a laptop or desktop application (e.g., for mobile or non-mobile devices running Windows PC, Mac OS PC, etc.), or a web application running in the user's browser or other internet access application. In another implementation, processing may be done solely on a server with which the program application interfaces. The application may be used to present the user interface on the user device, receive subject data parameters (textual, Images, video, sensor information, etc.) as input, and display results of the processing to the user. In another implementation, processing may be done on either the user device or the server depending on the current situation (i.e., considering parameters such as bandwidth, processing power available on the user device and server, etc.). Processors on any of the computing devices in the system may execute program instructions stored in memory of the computing device to perform the actions described herein.

In various storage configurations, the VTKB 108 and other data stores may reside on the user device, on the server, on a virtual machine, or in the cloud or another distributed computing environment. Replicas of the VTKB 108 and other data stores may be located on both the user device and the server. These can be the same or different replicas. For example, a user device VTKB 108 replica can contain a data subset of the full set existing on the server.

In some implementations, the system may include the components for performing the virtual treatment procedures in a treatment selection platform designed to help users make a decision about undergoing various aesthetic procedures, and to improve the overall experience during a selected aesthetic procedure. The system may include the application supporting virtual treatment procedures as described above. Two or more versions of this application may support different sets of requirements needed by separate groups of users: for example, one version may support doctors performing the treatment, and another version may support potential customers thinking of undergoing the procedure.

The system may include a doctors/practices registry, which may be a data store maintaining records of all the practices in a geographic region (e.g., a municipality, a state, a country, worldwide) that perform a particular aesthetic procedure. In accordance with or separately from the registry, the system may implement a digital procedures marketplace, which may be a distributed platform including various websites, web and/or mobile applications, data stores, account management and security frameworks, and other components for distributed and/or networked online platforms, and may further implement the virtual treatment procedures platform. The digital procedures marketplace may provide access to physicians, practices, and users, to communicate for the purpose of finding a desired aesthetic procedure and a practice to perform it. Practices may run sales targeted to specific users using some personalized parameters or their combinations (age/procedure required/face type, etc.).

A user seeking an aesthetic procedure may use any implementation of the above platform(s) by acquiring and executing the customer version of the application on a user device. With this application, the user can perform the virtual treatment procedure to (1) identify a suitable aesthetic procedure or combination of procedures that most effectively address(es) her aesthetic or therapeutic concerns, and/or (2) obtain information about any aesthetic procedure she is interested in. The user enters her information required (textual, images, sensory, etc.) into the application. The system then performs an implementation of the virtual treatment procedures specified herein. In one implementation, the user identifies a desired aesthetic procedure and the system performs the virtual treatment procedures for the desired aesthetic procedure. In other implementations, the system may identify one or more potential aesthetic procedures, based on the subject 202 characteristics and any other input from the user, such as treatment goals (e.g., eliminate one inch from waistline). The system may generate projected results for one or more of the identified procedures, and in some embodiments may first present the identified potential aesthetic procedures to the user for review and selection, then generate projected results for the selected aesthetic procedures. The system may then present the projected results to the user via the user interface as described above.

If the user is interested in undergoing the actual procedure (or one or more of the identified procedures), she can input a request to the application to scan all local practices in the practices registry, and display all the current offers\sales for the selected aesthetic procedure(s). She can allow the application to use her anonymized personal information to receive targeted offers from nearby practices. If the user selects an offer, she can schedule her visit or phone call with the selected practice right from the application. After she has completed the aesthetic procedure, the user can keep track of her progress with the application, such as by making images of herself on a daily basis; these collected progress images may be transmitted to the system for storage, such as in the VTKB 108, and may be stored locally on the user device and played back as a video to see the changes in motion. The user can also use the application to keep in touch with the doctor\practice that performed the procedure.

In another implementation where the user is a prospective customer of an aesthetic practice or facility, the user may submit the baseline images to the system via email to a specified email address. The system may process the baseline images and generate the projected results as above. In one embodiment, the system may respond to the email with a reply email that includes the projected results and marketing materials such as a report identifying providers of the procedure. In another embodiment, the system may respond to the user via e-mail with a link directing the user to an interactive web site displaying her virtual therapy results in a user interface that allows the user to adjust parameters of the virtual treatment. The system receives the parameter adjustments, generates new projected results if necessary, and delivers them to the web site. In another embodiment, the system may deliver the projected results to the user via e-mail with both attached estimated post-treatment images and a link directing the user to an interactive web site as described above.

A user that is a physician may use any implementation of the above platform(s) by acquiring and executing the physician version of the application on a user device. With this application, the physician can perform the virtual treatment procedures on a subject when the subject is in the physician's office. The physician version of the application may provide additional controls, relatively to the customer version, which allow adjustments of the processing to match every person's features. Doctor or doctor's office desk persons can receive potential candidate's requests through the application, installed on an office computing device or on the doctor's smartphone or other personal device. In addition, they can run their sales campaigns through the same media.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this invention.

What is claimed is:

1. A computing device for electronically generating virtual treatment results of a subject, the computing device comprising:
   memory storing program instructions and one or more sets of treatment parameters, each of the one or more sets being associated with a corresponding aesthetic procedure of a plurality of aesthetic procedures; and
   a processor that accesses the memory and executes the program instructions to:
      receive a baseline image depicting a first treatment area of a subject;
      identify, based on the corresponding treatment parameters of a first set of the one or more sets of treatment parameters, one or more zones of the baseline image, the first set being associated with a first aesthetic procedure of the plurality of aesthetic procedures;
      transform the baseline image within the one or more zones using the first set of treatment parameters to produce a first post-treatment image that depicts an estimated appearance of the first treatment area after the first treatment area is treated with the first aesthetic procedure; and
      display the baseline image and the first post-treatment image to the user.

2. The computing device of claim 1, wherein to identify the one or more zones, the processor executes the program instructions to:
   detect a face in the baseline image;
   detect a plurality of fiducial points on the baseline image based on the detected face; and
   juxtapose the face with a deformable vector model comprising a plurality of polygons and a plurality of polylines defining vertices of the vector model, the vertices including the plurality of fiducial points, to produce the one or more zones.

3. The computing device of claim 1, wherein to transform the baseline image within the one or more zones, the processor executes the program instructions to:
   identify a plurality of feature zones associated with the first aesthetic procedure;
   determine that a first feature zone of the plurality of feature zones corresponds to a first zone of the one or more zones of the baseline image; and
   modify image data of the baseline image within the first zone using a sequence of image manipulation techniques identified by the first set of transformation parameters, the sequence of image manipulation techniques being associated with the first feature zone.

4. The computing device of claim 3, wherein the image manipulation techniques include:
   a directional local filtration and a subsequent high frequency restoration of some or all of the image data; and
   a distortion effect to move the image data at an edge of a first zone of the one or more zones.

5. The computing device of claim 1, wherein the processor produces the first post-treatment image to depict the estimated appearance of the first treatment area a first period of time after the first treatment area is treated with the first aesthetic procedure, and wherein the processor further executes the program instructions to:
   transform the baseline image within the one or more zones using the first set of treatment parameters to produce a second post-treatment image that depicts the estimated appearance of the first treatment area a second period of time after the first treatment area is treated with the first aesthetic procedure, the second period of time being longer than the first period of time; and
   display the baseline image, the first post-treatment image, and the second post-treatment image to the user sequentially to show a treatment progression of the first aesthetic procedure results.

6. The computing device of claim 5, wherein the memory further stores a set of aging parameters, and wherein the processor further executes the program instructions to:
   identify, based on the set of aging parameters, one or more aging zones of the baseline image;
   transform the baseline image within the one or more aging zones using the set of aging parameters to produce:
      a first aged image that depicts aging effects accumulated on the first treatment area during the first period of time after the baseline image was captured; and
      a second aged image that depicts aging effects accumulated on the first treatment area during the second period of time after the baseline image was captured; and
   display a user interface containing a plurality of virtual procedure images including the baseline image, the first post-treatment image, the second post-treatment image, the first aged image, and the second aged image, the user interface enabling a user of the computing device to view an aging progression and the treatment progression by changing which of the plurality of virtual procedure images is displayed.

7. The computing device of claim 1, wherein the computing device further comprises a display and a user input device each in communication with the processor, and wherein the processor further executes the program instructions to present a user interface to the user via the display and the user input device, the user interface enabling the user to provide user input to the processor.

8. The computing device of claim 7, wherein the user input is a modification to the one or more zones, and responsive to receiving the user input, the processor executes the program instructions to adjust a perimeter of a first zone of the one or more zones according to the user input.

9. The computing device of claim 7, wherein the user input is a treatment goal, and responsive to receiving the user input, the processor executes the program instructions to determine that the first aesthetic procedure is associated with the treatment goal.

10. The computing device of claim 1, wherein the first set of treatment parameters are determined to transform a pre-treatment image into a post-treatment image, the pre-treatment image depicting a treatment area of a model and captured before the treatment area is treated with the first aesthetic procedure, and the post-treatment image depicting the treatment area of the model and captured after the treatment area is treated with the first aesthetic procedure.

11. A system, comprising:
   a server storing a virtual treatment knowledge base; and
   a program application installed on a plurality of user devices in electronic communication with the server, the program application configuring each of the plurality of user devices to cooperate with the server to create a virtual treatment procedures platform;

the program application further configuring a first user device of the plurality of user devices to:
receive a baseline image depicting a first treatment area of a subject;
transform the baseline image using a plurality of transformation parameters to produce a first post-treatment image that depicts an estimated appearance of the first treatment area after the first treatment area is treated with a first aesthetic procedure; and
display the baseline image and the first post-treatment image on the first user device.

12. The system of claim 11, wherein the server further stores a virtual treatment learning engine that, when executed, configures the server to:
receive a pre-treatment image depicting a second treatment area of a model before the second treatment area is treated with the first aesthetic procedure;
receive a post-treatment image depicting the second treatment area after the second treatment area is treated with the first aesthetic procedure;
determine that the plurality of transformation parameters transforms the pre-treatment image into the post-treatment image; and
store the plurality of transformation parameters in the virtual treatment knowledge base; and
wherein the program application further configures the user devices to receive the plurality of transformation parameters from the server.

13. The system of claim 12, wherein:
the program application further configures the first user device to:
receive identifying information of the subject; and
send the identifying information to the server; and
the server is further configured to:
determine, based on the identifying information, that the subject is similar to the model; and
responsive to a determination that the subject is similar to the model, send the plurality of transformation parameters to the first user device.

14. The system of claim 13, wherein to receive the identifying information, the program application configures the first user device to retrieve the identifying information from a source that is external to the system and is in electronic communication with the first user device.

15. The system of claim 11, further comprising a practices registry implemented as an electronic data store accessible by the server, the practices registry including a plurality of practice records each associated with a corresponding practice of a plurality of practices that perform the first aesthetic procedure and are located in a selected geographic area, the server being configured to retrieve practice information from one or more of the plurality of practice records and send the practice information to the first user device.

16. The system of claim 15, wherein a second user device of the plurality of user devices is controlled by a first practice of the plurality of practices, and wherein the program application further configures the first user device to:
receive a first user input on an input device of the first user device;
determine that the first user input is a request to view the practice information;
receive the practice information from the server;
display the practice information on a display of the first user device;
receive a second user input on the input device;
determine that the second user input is a selection, from the practice information, of an offer by the first practice to perform the first aesthetic procedure; and
communicate with the second user device to schedule an appointment for the subject with the first practice.

17. The system of claim 11, wherein the program application configures the first user device to, prior to transforming the baseline image:
receive a first user input on an input device of the first user device;
determine that the first user input comprises one or more treatment goals; and
determine that the first aesthetic procedure is associated with the one or more treatment goals.

18. A method for providing an electronic visualization of a virtual treatment on a treatment area of a subject, the method comprising:
receiving, by a computing device, a baseline image depicting the treatment area;
receiving, by the computing device, a plurality of transformation parameters associated with an aesthetic procedure;
transforming, by the computing device, the baseline image using the plurality of transformation parameters to produce a first post-treatment image that depicts an estimated appearance of the treatment area after the treatment area is treated with the aesthetic procedure; and
displaying, by the computing device in a user interface of the computing device, the baseline image and the first post-treatment image.

19. The method of claim 18, wherein receiving the plurality of transformation parameters comprises:
determining an identifying parameter of the subject;
matching the identifying parameter of the subject to a model identifying parameter stored in a model treatment results record, the model treatment results record comprising a plurality of model transformation parameters for transforming a pre-treatment image of the model to a post-treatment image of the model; and
obtaining the plurality of model transformation parameters as the plurality of transformation parameters.

20. The method of claim 18, further comprising:
before receiving the plurality of transformation parameters:
receiving, by the computing device, a first user input comprising one or more treatment goals; and
determining, by the computing device, that the one or more treatment goals are associated with the aesthetic procedure and with a plurality of potential aesthetic procedures;
receiving, by the computing device, a plurality of sets of potential transformation parameters, each set associated with a corresponding potential aesthetic procedure of the plurality of potential aesthetic procedures;
transforming, by the computing device, the baseline image using each set of the plurality sets of potential transformation parameters to produce a corresponding potential post-treatment image of a plurality of potential post-treatment images each depicting the estimated appearance of the treatment area after the treatment area is treated with the corresponding potential aesthetic procedure;
further displaying, by the computing device in the user interface of the computing device, the plurality of potential post-treatment images, the user interface enabling a user of the computing device to select one or more of the baseline image, the first post-treatment image, and one or more of the plurality of potential post-treatment images for display;

receiving, by the computing device, a second user input comprising a selection of the first post-treatment image; and sending, by the computing device to a server in electronic communication with the computing device, information identifying the subject and the aesthetic procedure.

* * * * *